US011308590B2

(12) United States Patent
Nosher et al.

(10) Patent No.: US 11,308,590 B2
(45) Date of Patent: Apr. 19, 2022

(54) COMPUTATIONAL ULTRASOUND FOR IMPROVED LIVER AND KIDNEY CANCER DIAGNOSIS

(71) Applicant: Rutgers, The State University of New Jersey, New Brunswick, NJ (US)

(72) Inventors: John Nosher, Basking Ridge, NJ (US); Ilker Hacihaliloglu, Jersey City, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 127 days.

(21) Appl. No.: 16/489,151

(22) PCT Filed: Feb. 27, 2018

(86) PCT No.: PCT/US2018/019945
§ 371 (c)(1),
(2) Date: Aug. 27, 2019

(87) PCT Pub. No.: WO2018/157130
PCT Pub. Date: Aug. 30, 2018

(65) Prior Publication Data
US 2020/0065948 A1 Feb. 27, 2020

Related U.S. Application Data

(60) Provisional application No. 62/464,058, filed on Feb. 27, 2017.

(51) Int. Cl.
*G06T 5/10* (2006.01)
*G06T 5/00* (2006.01)
(Continued)

(52) U.S. Cl.
CPC ............ *G06T 5/008* (2013.01); *A61B 8/5207* (2013.01); *G06T 5/10* (2013.01); *G06T 5/20* (2013.01);
(Continued)

(58) Field of Classification Search
None
See application file for complete search history.

(56) References Cited

U.S. PATENT DOCUMENTS

2009/0136104 A1   5/2009  Hajian et al.
2013/0324785 A1*  12/2013 Bertram ................. G06T 15/06
                                                                600/1
2016/0217563 A1   7/2016  Wahrenberg

FOREIGN PATENT DOCUMENTS

WO        2009056857 A1    5/2009

OTHER PUBLICATIONS

Jakia Afruz, Frequency Domain Pseudo-color to Enhance Ultrasound Images, Nov. 2010, vol. 3, No. 4, Computerand Information Science, p. 24-34 (Year: 2010).*

(Continued)

*Primary Examiner* — Randolph I Chu
(74) *Attorney, Agent, or Firm* — Fox Rothschild LLP

(57) ABSTRACT

This disclosure provides a system and method for generating an ultrasound image. The method includes receiving a raw ultrasound signal output from an ultrasound device and performing operations to transform the raw ultrasound signal into an enhanced ultrasound image. The enhanced ultrasound image may be further processed by radial symmetry filtering to generate a radial symmetry image. Both the enhanced image and the radial symmetry image can be by a medical practitioner to make a liver or kidney cancer diagnosis exclusively based on ultrasound data.

20 Claims, 8 Drawing Sheets

(51) Int. Cl.
*A61B 8/08* (2006.01)
*G06T 5/20* (2006.01)
(52) U.S. Cl.
CPC .............. *G06T 2207/10132* (2013.01); *G06T 2207/30056* (2013.01)

(56) References Cited

OTHER PUBLICATIONS

Belaid et al. "α Scale spaces filters for phase based edge detection in ultrasound images", Conference: 2014 IEEE 11th International Symposium on Biomedical Imaging (ISBI 2014) (Year: 2014).*
Simonyan, K et al., "Very Deep Convolutional Networks For Large-Scale Image Recognition", ICLR 2015 Conference, Apr. 10, 2015, pp. 1-14.
He, K. et al., "Deep Residual Learning for Image Recognition", Dec. 12, 2015, pp. 1-12.
Szegedy, C. et al., "Rethinking the Inception Architecture for Computer Vision", Dec. 11, 2015.
NPL to Pawlicki et al.: "Method for Estimating Total Attenuation from A Spatial Map of Attenuation Slope for Quantitative Ultrasound Imaging", In: Ultrason Imaging. Apr. 2013, vol. 35, No. 2, Mar. 25-26, 2006 [online] [retrieved on Apr. 26, 2018 (Apr. 26, 2018)] Retrieved from the Internet <URL: https://www.ncbi.nlm.nih.gov/pubmed/23493614>, entire document.
Mwikirize, et al: "Enhancement of Needle Tip and Shaft from 2D Ultrasound Using Signal Transmittal Maps", Oct. 2, 2016, Big Data Analytics in the Social and Ubiquitous Context: 5th International Workshop on Modeling Social Media, MSM 2014, 5th International Workshop on Mining Ubiquitous and Social Environments, Muse 2014 and First International Workshop on Machine LE, XP047359580, ISBN: 978-3-642-17318-9 [retrieved on Oct. 2, 2016].
Hacihaliloglu et al: "Projection-Based Phase Features for Localization of a Needle Tip in 2D Curvilinear Ultrasound", 18th International Conference, Munich, Germany, Oct. 5-9, 2015, Proceedings, Part I in: "Lecture Notes in Computer Science", 2015, Springer Berlin Heidelberg, Berlin Germany, XP055779149, ISSN: 0302-9743, ISBN: 978-3-030-67069-6, vol. 9349, pp. 347-354, DOI: 10.1007/978-3-319-24553-9_43, Retrieved from the Internet URL: <http://link.springer.com/content/pdf/10.1007/978-3-319-24553-9_43>.
Prevost, et al: "Automatic detection and segmentation of renal lesions in 3D contrast-enhanced ultrasound images", Optoelectronic Signal Processing For Phased-Array Antennas IV, [Online] vol. 8314, Feb. 10, 2012, p. 83141D, XP055778880, 1000 20th St. Bellingham WA 98225-6705 USA, ISSN: 0277-786X-DOI: 10.1117/12.911103, ISBN: 978-1-5106-4277-5, Retrieved from the Internet: URL <https://hal.archives-ouvertes.fr/hal-00703131/document>.
Karamalis, et al: "Ultrasound conference maps using random walks", Medical Imae Analysis, Aug. 2012, vol. 16, No. 6, pp. 1101-1112, XP055379021, GB, ISSN: 1361-8415, DOI: 10.1016/j.media.2012.07.005.
Hughes, et al: "Automatic Attenuation Compensation for Ultrasonic Imaging", 1997, Ultrasound in Medicine & Biology, vol. 23, No. 5, pp. 651-664, XP055304486, US, ISSN: 0301-5629, DOI: 10.1016/S0301-5629(97)00002-1.

* cited by examiner

FIG. 4A
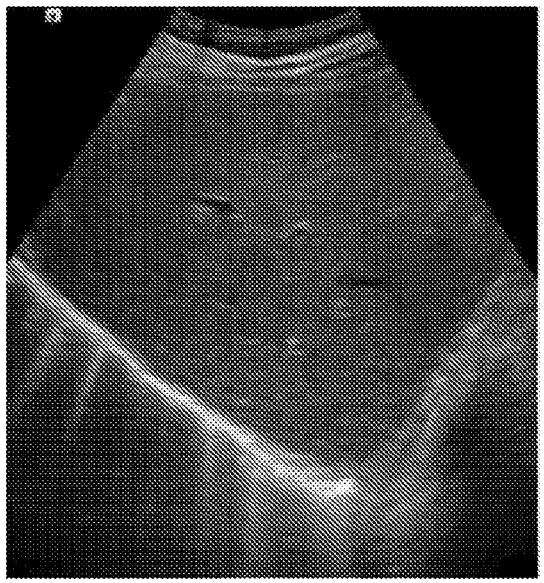
Normal/Healthy Liver
FIG. 4B
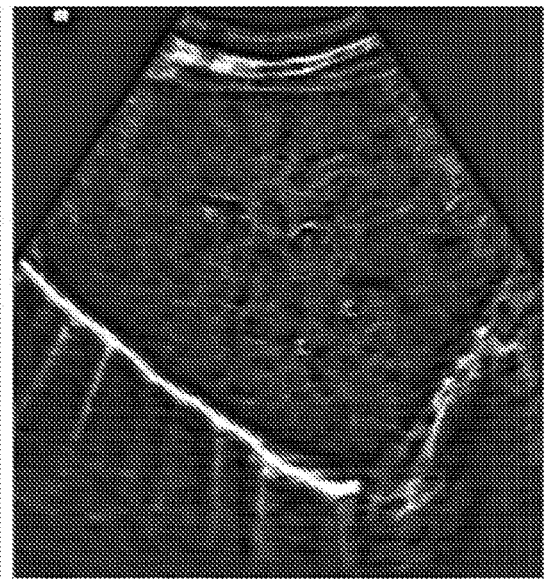
Enhanced Normal/Healthy Liver
FIG. 4C
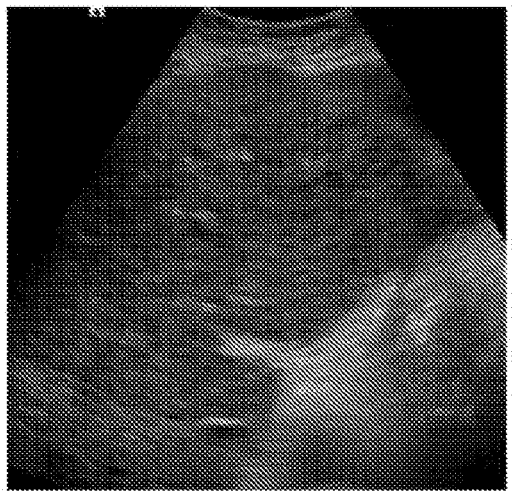
Diseased Liver
FIG. 4D
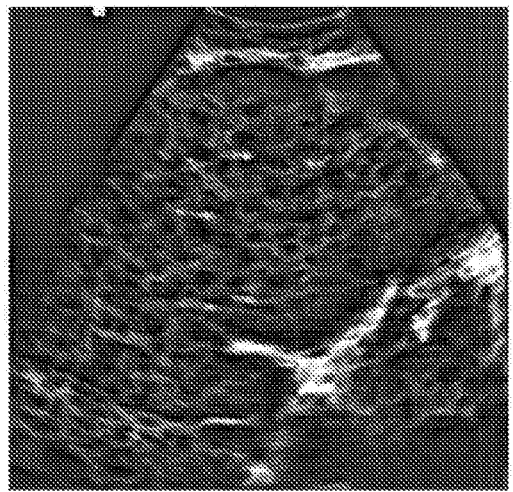
Enhanced Diseased Liver
*FIG. 4*

Normal Liver
FIG. 5A
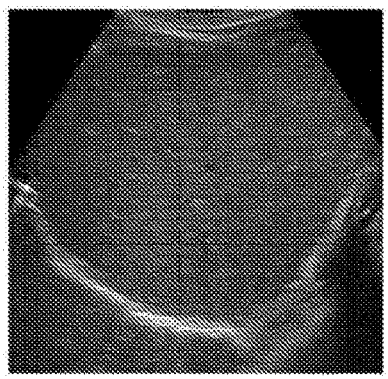
FIG. 5B
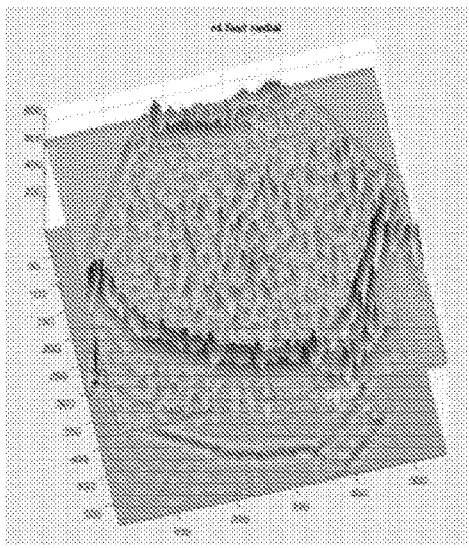
FIG. 5C
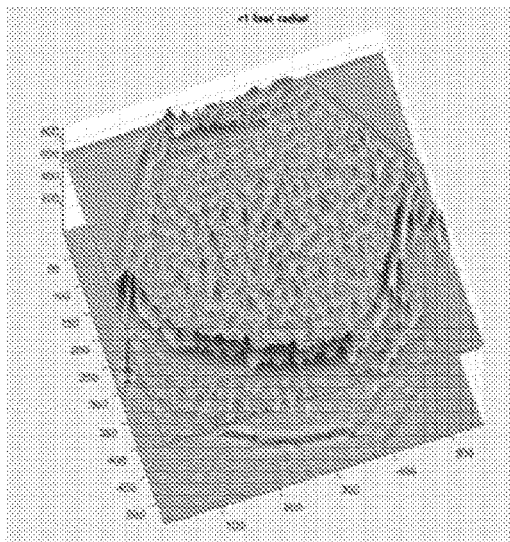
FIG. 5D
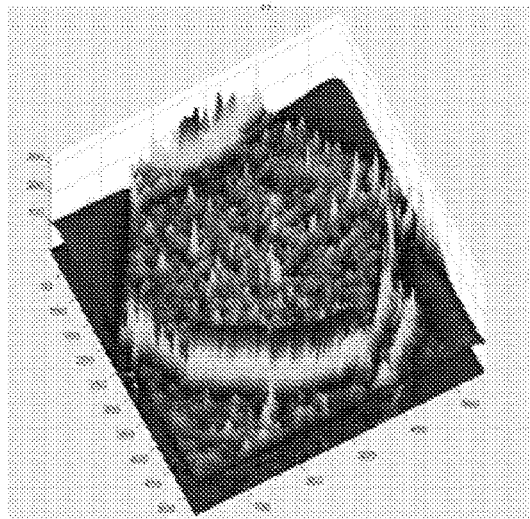
FIG. 5E
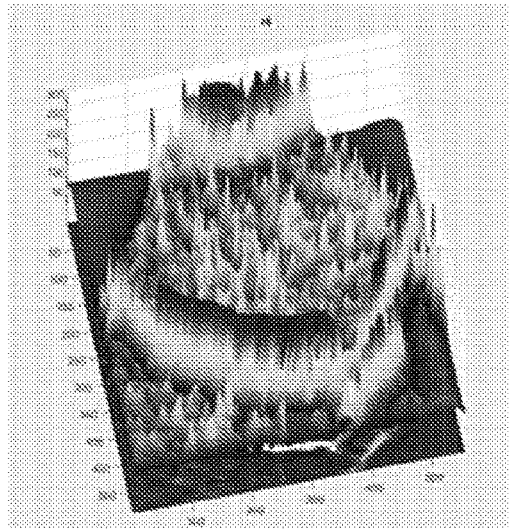
*FIG. 5*

FIG. 6A
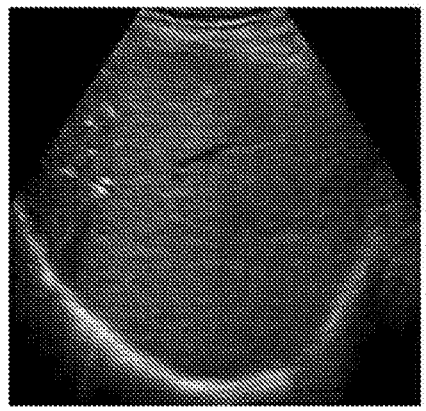
Diseased Liver
FIG. 6B
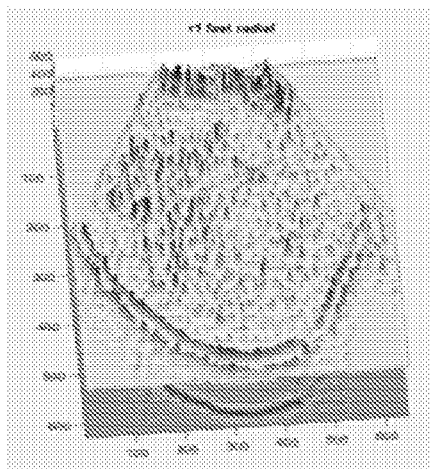
FIG. 6C
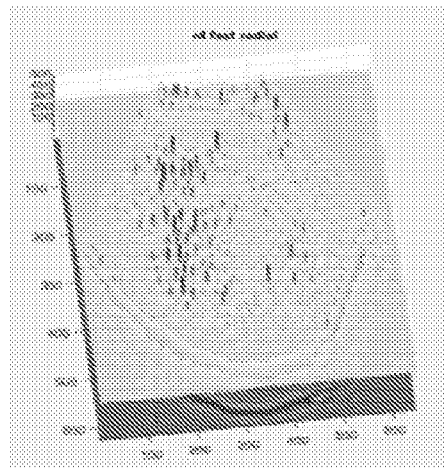
FIG. 6D
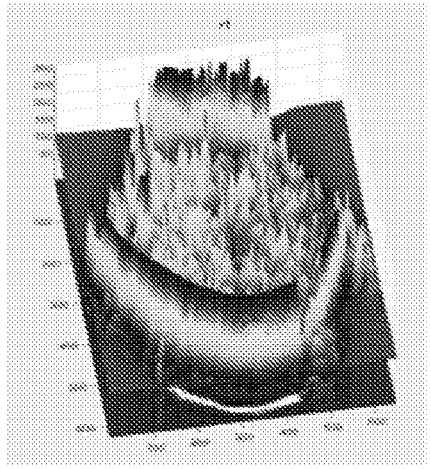
FIG. 6E
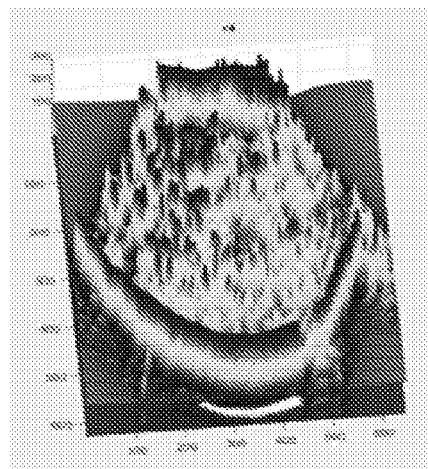
*FIG. 6*

COMPUTATIONAL ULTRASOUND FOR IMPROVED LIVER AND KIDNEY CANCER DIAGNOSIS

CROSS-REFERENCE TO RELATED APPLICATIONS

This application is the U.S. National Phase of International Patent Application Ser. No. PCT/US2018/019945, filed Feb. 27, 2018, which claims priority under 35 U.S.C. § 119(e) to U.S. Provisional Patent Application No. 62/464,058, filed Feb. 27, 2017. The foregoing applications are incorporated by reference herein.

FIELD

This document relates generally to image processing. More particularly, this document relates to systems and methods for ultrasound image processing facilitating improved cancer diagnosis and treatment monitoring.

BACKGROUND

Hepatitis C Virus ("HCV") and Non-Alcoholic Fatty Liver Disease ("NAFLD") are the two most common causes of chronic liver disease in North America. It is probably the most common type of liver disease in the United States. In clinical practice, transabdominal ultrasound is most widely used as an initial imaging modality because of its availability, low cost, and no radiation exposure. NAFLD may lead to fibrosis, cirrhosis, liver cancer, liver failure requiring a liver transplant, and mortality. Abdominal ultrasound cannot detect mild hepatic steatosis and cannot differentiate simple steatosis, nonalcoholic steatohepatitis (NASH), and hepatic fibrosis. It is operator dependent, interfered by intra-abdominal gas and technically difficult with poor image quality in obese patients.

SUMMARY

The present disclosure provides systems and methods for generating enhanced ultrasound images. The ultrasound images processed by the present systems and methods show a soft tissue pattern having a level of visual clarity that enables a medical practitioner to make a liver or kidney disease diagnosis based solely on ultrasound data, without the need of biopsy samples.

In one aspect, the system may include a non-transitory, computer-readable memory, one or more processors and a computer-readable medium containing programming instructions. The programming instructions, when executed by the one or more processors, cause the system to acquire a raw ultrasound signal output from an ultrasound device and generate filtered ultrasound image data by filtering the raw ultrasound signal to transform information from a signal domain to a frequency domain. The system may also extract image phase and energy features from the filtered ultrasound image data and generate a filtered ultrasound signal by transforming the image phase and energy features from the frequency domain to the signal domain. The system may further produce a transmission map estimation based on a backscattered ultrasound signal from a tissue interface and enhance the image phase and energy features of the filtered ultrasound signal based on the transmission map estimation so that portions of a soft tissue associated therewith are made darker or lighter in an enhanced ultrasound image.

In some embodiments, the system may perform radial symmetry filtering on the enhanced ultrasound image by analyzing dark spherical shapes in the enhanced ultrasound image and generate a radial symmetry image to identify regions of interest in the enhanced ultrasound image. In some embodiments, the system may additionally output a surface topography map based on the radial symmetry image. In some embodiments, the step of generating the filtered ultrasound image data is performed by a Fourier transform. In some embodiments, the step of generating the filtered ultrasound signal is performed by the inverse Fourier transform.

In some embodiments, the step of extracting the image phase and energy features is performed by an alpha scale filtering. In some embodiments, the alpha scale filtering is performed in a frequency domain, and the alpha scale filtering can be defined by expression $$ASF(\omega) = \begin{cases} n_c \omega^a \exp(-(\sigma\omega)^{2\alpha}) & \omega > 0 \\ 0 & \text{otherwise} \end{cases}$$

where $\alpha$ is constant derivative parameter, $\sigma$ is a filter alpha-scale parameter, and $n_c$ is a unit normalization constant calculated from filter $\alpha$. $n_c$ is computed in accordance with mathematical equation $$n_c = 2 \frac{\sqrt{\pi\alpha}\, 2^{\frac{2a+1}{4\alpha}} s^{a+0.5}}{\sqrt{\Gamma\left(\frac{2a+1}{2\alpha}\right)}}$$

where s is a scale parameter and a is a derivative parameter.

In some embodiments, the transmission map estimation comprises combining scattering and attenuation effects in soft tissue based on equation $$US(x,y) = US_A(x,y) US_E(x,y) + (1 - US_A(x,y))\alpha$$

where US(x,y) is a local energy image, $US_A(x,y)$ is a signal transmission map, $US_E(x,y)$ is an enhanced ultrasound image, and $\alpha$ is a constant value representative of echogenicity in the soft tissue in a local region. $US_E(x,y)$ can be extracted by estimating the signal transmission map $US_A(x,y)$ using a Beer-Lambert law which models an attenuation function as a function of imaging depth. The Beer-Lambert law is defined by equation $$US_T(x,y) = US_o(x,y) \exp(-\eta d(x,y))$$

where $US_o(x,y)$ is an initial intensity image, $US_T(x,y)$ is an attenuated intensity image, $\eta$ is an attenuation coefficient, and d(x,y) is a distance from an ultrasound transducer surface. $US_A(x,y)$ is obtained by minimizing an objective function defined by equation $$\frac{\lambda}{2} \|US_A(x,y) - US_T(x,y)\|_2^2 + \sum_{j \in \omega} \|W_j o (D_j * US_A(x,y))\|_1$$

where $\omega$ is an index set, o represents element wise multiplication, * is a convolution operation, $D_j$ is obtained using a bank of high order differential filters consisting of eight Kirsch filters and one Laplacian filter, and $W_j$ is a weighting matrix calculated in accordance with mathematical equation $$W_j = \exp(-|D_j(x,y) * US(x,y)|^2)$$

$US_E(x,y)$ is calculated in accordance with equation $$US_E(x, y) = \left[\frac{US(x, y) - \alpha}{[\max(US_A(x, y), \varepsilon)]^\delta}\right] + \alpha.$$

In some embodiments, the radial symmetry filtering is specified by equation $$S_n = F_n * A_n$$

where "*" denotes the convolution operation; $A_n$ is an isotropic Gaussian function and $F_n$ is defined as:

$$F_n(p) = \frac{M_n(p)}{k_n}\left(\frac{|\tilde{O}_n(p)|}{k_n}\right)\alpha$$

$$\tilde{O}_n(p) = \begin{cases} \tilde{O}_n(p), & O_n(p) < k_n \\ k_n, & \text{otherwise} \end{cases}$$

and $\alpha$ is a radial strictness parameter, and $k_n$ is a scaling factor across different radii. The radial symmetry image is defined by equation $$S = \frac{1}{|N|}\sum_{n \in N} S_n$$

where S is a sum of all symmetry contributions over all ranges considered.

In another aspect, a method for generating an ultrasound image is also provided. The method includes acquiring, by a computing device, a raw ultrasound signal output from an ultrasound device and generating filtered ultrasound image data by filtering the raw ultrasound signal to transform information from a signal domain to a frequency domain. The method also includes extracting image phase and energy features from the filtered ultrasound image data and generating a filtered ultrasound signal by transforming the image phase and energy features from the frequency domain to the signal domain. The method further includes producing a transmission map estimation based on a backscattered ultrasound signal from a tissue interface and enhancing the image phase and energy features of the filtered ultrasound signal based on the transmission map estimation so that portions of a soft tissue associated therewith are made darker or lighter in an enhanced ultrasound image.

In some embodiments, the method further includes performing radial symmetry filtering on the enhanced ultrasound image by analyzing dark spherical shapes in the enhanced ultrasound image and generating a radial symmetry image to identify regions of interest in the enhanced ultrasound image. In some embodiments, the method additionally includes outputting a surface topography map based on the radial symmetry image.

DESCRIPTION OF THE DRAWINGS

The present solution will be described with reference to the following drawing figures, in which like numerals represent like items throughout the figures.

FIGS. 4A-D (collectively "FIG. 4") show a B-mode (original) ultrasound image of a normal/healthy liver (FIG. 4A) and an enhanced ultrasound image (FIG. 4B) of a normal/healthy liver, and a B-mode (original) ultrasound image (FIG. 4C) of a diseased liver and an enhanced ultrasound image (FIG. 4D) of a diseased liver.

FIGS. 5A-E (collectively "FIG. 5") show a comparison of different image types; FIG. 5A shows a B-mode (original) ultrasound image of a normal/healthy liver; FIG. 5B shows surface topography visualization of a radial symmetry image corresponding to normal/healthy liver tissue; FIG. 5C shows surface topography visualization of a radial symmetry image corresponding to normal/healthy liver tissue, with different radial symmetry filter parameters applied as compared to FIG. 5B; and FIG. 5D shows surface topography visualization of an enhanced ultrasound image corresponding to normal/healthy tissue; FIG. 5E shows surface topography visualization of an enhanced ultrasound image corresponding to normal/healthy tissue, with different filter parameters used as compared to FIG. 5D.

FIGS. 6A-E (collectively "FIG. 6") show a comparison of different image types; FIG. 6A shows a B-mode (original) ultrasound image of a diseased liver; FIG. 6B shows surface topography visualization of a radial symmetry image corresponding to diseased liver tissue; FIG. 6C shows surface topography visualization of a radial symmetry image corresponding to diseased liver tissue, with different radial symmetry filter parameters applied as compared to FIG. 6B; and FIG. 6D shows surface topography visualization of an enhanced ultrasound image corresponding to diseased tissue; FIG. 6E shows surface topography visualization of an enhanced ultrasound image corresponding to diseased tissue, with different filter parameters used as compared to FIG. 6D.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present solution concerns systems and methods for ultrasound image processing and design of a next-generation ultrasound imaging platform in the context of cancer diagnosis and treatment monitoring with a specific focus on kidney and liver. The ultrasound image processing of the present solution uses a raw ultrasound signal to extract image features from filtered ultrasound data. Previous platforms use image data. These previous platforms suffer from many drawbacks. For example, these previous platforms experience issues due to poor sensitivity and specificity for kidney and liver cancer detection which causes major problems in the management and treatment of cancer. In general, imaging appearances of liver metastases are nonspecific, and biopsy specimens are required for histologic diagnosis. The present solution resolves these drawbacks by implementing a new computational algorithm as described herein in an ultrasound device.

Figure 3:
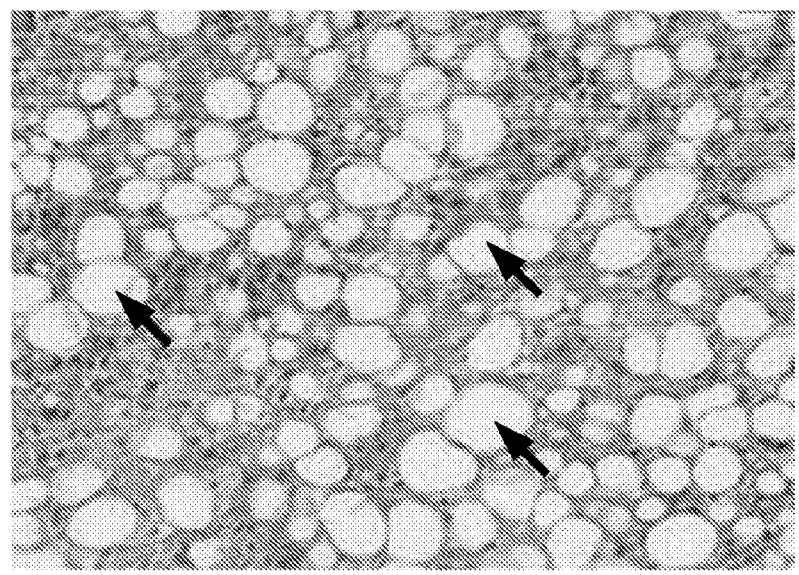
FIG. 3 shows a biopsy (histopathology) image of a non-healthy liver indicating a fatty liver disease.

A biopsy (histopathology) image of a non-healthy liver indicating a fatty liver disease is shown in FIG. 3. The circular pattern in the biopsy image, as highlighted by arrows, indicates that the liver has a fatty liver disease. However, the circular pattern is not visible or detectable by investigating an ultrasound image. Accordingly, the diagnosis of a disease is complicated based on ultrasound images. There is a need for an image processing device which can enhance the ultrasound data and provide more information useful for making a diagnosis. Such a method is implemented by the present solution.

In some scenarios, the present solution is used for early detection of fatty liver, liver cancer, and kidney cancer. Biopsies are current the standard technique for such early detection. The present solution does not require obtaining a sample by performing a biopsy. Accordingly, the present solution allows for earlier detection and for detection without unduly stressing the patient.

The present invention combines different steps in order to create the framework that results in the enhancement of the liver and/or kidney ultrasound data. Optimization of each of the steps is also one of the main contributions. The main part of the algorithm is based on the extraction of local phase image features from liver and kidney ultrasound data. Phase-based image enhancement and processing has been previously proposed to process various medical image data. Image phase information is a key component in the interpretation of a scene that has long been known to contribute more to the visual appearance of an image than magnitude information. Phase features are intensity invariant and more robust to noise which are important characteristics especially for processing ultrasound images. Extraction of phase information is performed in the frequency domain where the B-mode ultrasound image (original image) is transformed to the frequency domain by Fourier transform operation and multiplied with a band-pass quadrature filter.

Figure 1:
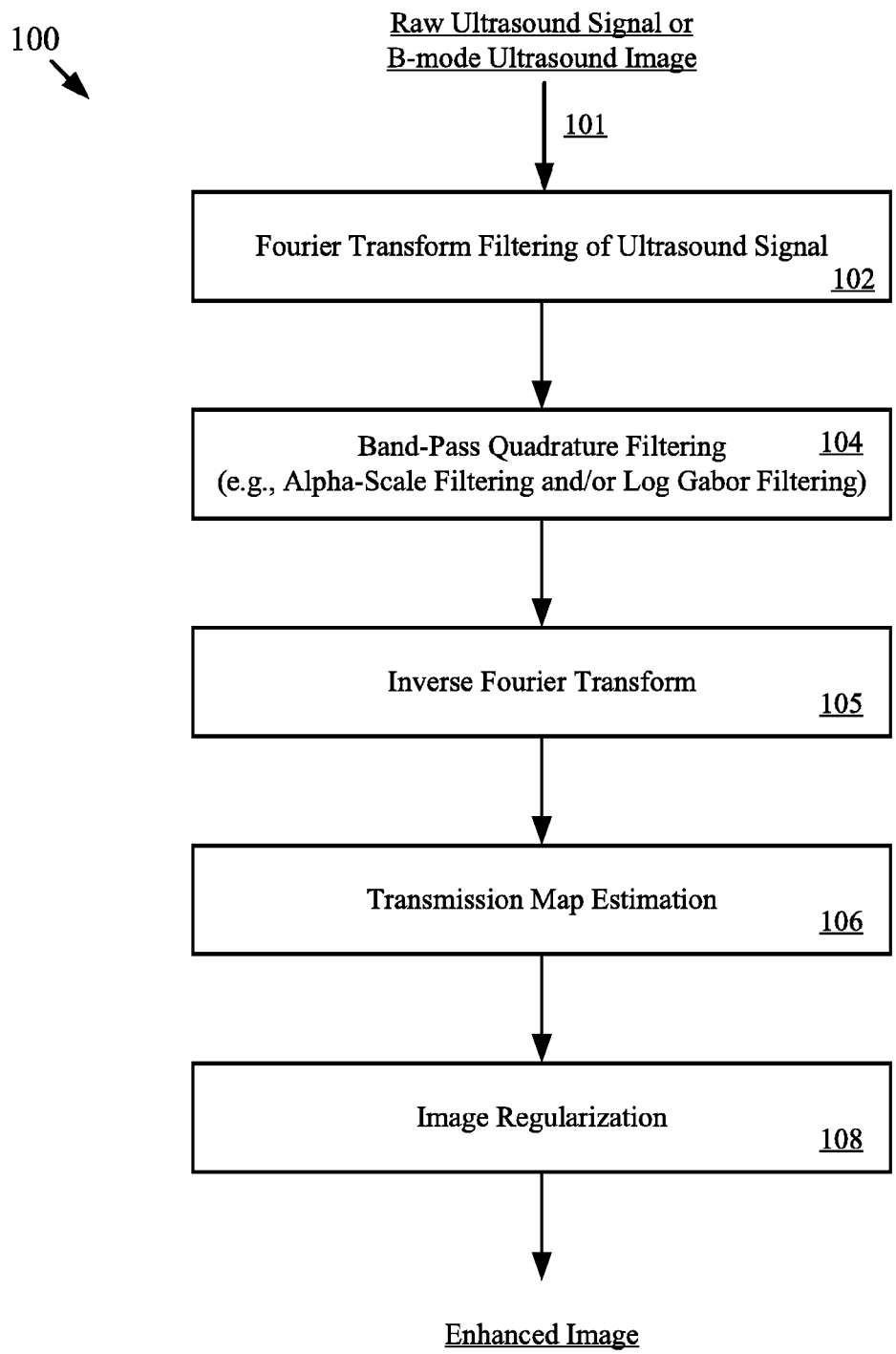
FIG. 1 shows an example of a process for generating an enhanced ultrasound image.

Referring now to FIG. 1, there is provided an illustration of an exemplary method 100 for image enhancement that is useful for understanding the present solution. The combination of the operations of steps 102-108 creates a framework resulting in the enhancement of liver and/or kidney ultrasound data.

The main part of the process is based on the extraction of local phase image features from an ultrasound signal. Image phase information is a key component in the interpretation of a scene since it contributes more to the visual appearance of an image than magnitude information. Phase features are intensity invariant and more robust to noise which are important characteristics especially for processing ultrasound images.

Extraction of phase information is performed in the frequency domain where a raw ultrasound signal or a B-mode ultrasound image is received from an ultrasound device as shown by arrow 101. The raw ultrasound image signal is then transformed from a signal domain to a frequency domain, as shown by 102. A Fourier transform is used to achieve this transformation. Thereafter, the filtered ultrasound image data is multiplied with a band-pass quadrature filter, as shown by 104. Fourier transforms, and band-pass quadrature filters are well known in the art. Any known or to be known Fourier transform and/or band-pass quadrature filter can be used herein without limitation. For example, an optimized band-pass quadrature filter is employed in 104. Optimization is related to selection of filter parameters. Usually, this is performed by trial and error. Once a good set of parameters are found, these are kept constant, and all the ultrasound images are filtered with this optimized filter. However, automatic filter parameter optimization may be employed herein. Techniques for automatic filter parameter optimization is known in the art. Any known or to be known technique for automatic filter parameter optimization can be used herein without limitation.

In some scenarios, the band-pass quadrature filter comprises an alpha-scale filter. As such, alpha-scale filtering can be employed in 104. The alpha-scale filtering is performed to extract phase and energy features from a filtered raw ultrasound signal. This feature extraction facilitates the generation of an enhanced ultrasound image showing a soft tissue pattern having a level of visual clarity at which a medical practitioner is able to make a liver or kidney cancer diagnosis exclusively based on ultrasound data. Notably, other frequency domain quadrature filters (e.g., Log Gabor filter) are not suitable for use alone in liver and kidney diagnosis applications because such filtering does not result in enhanced soft tissue features.

It should be understood that Log Gabor filters are less computationally and resource intensive as compared to alpha-scale filters. Therefore, a person skilled in the art would not be motivated to use alpha-scale filters when processing ultrasound image data. However, the inventors recognized that the combination of alpha-scale filters with the other two Fourier transform process of 102 and transmission map filtering process of 106-108 provides certain non-obvious advantageous when interested in visualizing certain soft tissue features. These advantages include the enhancement of soft tissue features having a level of visual clarity at which a medical practitioner is able to make a liver or kidney cancer diagnosis exclusively based on ultrasound data.

In some scenarios, an alpha-scale filter in the frequency domain is constructed as defined by the following Equation (1):

$$SF(\omega) = \begin{cases} n_c \omega^a \exp(-(\sigma\omega)^{2\alpha}) & \omega \geq 0 \\ 0 & \text{otherwise} \end{cases} \quad (1)$$

where α is constant derivative parameter which is chosen to be α=0.2 in order for the filters to satisfy the DC condition. σ is the filter alpha-scale parameter (for example, in some embodiments, the filter alpha-scale parameter is 25), and $n_c$ is a unit normalization constant calculated from filter α value using the following Equation (2):

$$n_c = 2 \frac{\sqrt{\pi\alpha} \, 2^{\frac{2a+1}{4\alpha}} s^{a+0.5}}{\sqrt{\Gamma\left(\frac{2a+1}{2\alpha}\right)}} \quad (2)$$

where s is a scale parameter and a is a derivative parameter. In some embodiments, the scale parameter is 2, and the derivative parameter is 1.83.

Filtering the Fourier transformed ultrasound image with the constructed alpha scale filter and using an inverse Fourier transform operation, image phase, and energy features are extracted from the ultrasound image. The local energy image encodes the underlying structural information of the liver or kidney ultrasound image.

After completing the alpha scale filtering, method 100 continues with 105 where the ultrasound image data is transformed from the frequency domain to the signal domain via an inverse Fourier transform process. The results of 105 are then used in 106 to obtain a transmission map estimation. The interaction of the ultrasound signal within the tissue can be characterized into two main categories (namely, scattering and attenuation). Since the information of the backscattered ultrasound signal (from the tissue interface to the ultrasound transducer) is modulated by these two interactions, they can be viewed as mechanisms of structural information coding. Based on this a model was developed. The model is referred to herein as an ultrasound signal transmission map. The ultrasound signal transmission map is useful for recovering a pertinent liver and/or kidney tissue structure from the ultrasound images. In order to achieve this, a linear interpolation model is employed which combines scattering and attenuation effects in the tissue. The linear interpolation model is defined by the following Equation (3):

$$US(x,y)=US_A(x,y)US_E(x,y)+(1-US_A(x,y))\alpha \quad (3)$$

where $US(x,y)$ is the local energy image calculated in 104, $US_A(x,y)$ is the signal transmission map, $US_E(x,y)$ is the enhanced liver/kidney ultrasound image, and $\alpha$ is a constant value representative of echogenicity in the tissue in the local region. In the present solution, three different values for $\alpha$ are used to obtain three different enhancement results.

The local energy image generated in 104 is used in a subsequent filtering process as shown by 106 and 108. The filtering process of 106 and 108 is generally performed to enhance the extracted phase, and energy features so that portions of the soft tissue associated therewith are made darker or lighter in the enhanced ultrasound image (e.g., as shown in FIG. 3).

In 106, $US_E(x,y)$ is extracted by estimating the signal transmission map $US_A(x,y)$ using a well-known Beer-Lambert law which models the attenuation function as a function of imaging depth. The Beer-Lambert law is defined by the following Equation (4):

$$US_T(x,y)=US_o(x,y)\exp(-\eta d(x,y)) \quad (4)$$

where $US_o(x,y)$ is the initial intensity image (filtered image obtained from the alpha-scale filtering step), $US_T(x,y)$ is the attenuated intensity image, $\eta$ is the attenuation coefficient (for example, in some embodiments, the attenuation coefficient used is 2), and $d(x,y)$ is the distance from the ultrasound transducer surface.

Once $US_T(x,y)$ is obtained, $US_A(x,y)$ is obtained by minimizing an objective function defined by Equation (5):

$$\frac{\lambda}{2}\|US_A(x,y)-US_T(x,y)\|_2^2 + \sum_{j\in\omega}\|W_j o(D_j * US_A(x,y)\|_1 \quad (5)$$

where $\omega$ is an index set, $o$ represents element wise multiplication, and $*$ is a convolution operation. $D_j$ is obtained using a bank of high order differential filters consisting of eight Kirsch filters and one Laplacian filter. $W_j$ is a weighting matrix calculated using the following Equation (6):

$$W_j=\exp(-|D_j(x,y)*US(x,y)|^2) \quad (6)$$

Once $US_A(x,y)$ is estimated, $US_E(x,y)$ is calculated using the following Equation (7):

$$US_E(x,y) = \left[\frac{US(x,y)-\alpha}{[\max(US_A(x,y),\varepsilon)]^\delta}\right] + \alpha \quad (7)$$

FIG. 3 shows a biopsy (histopathology) image of a non-healthy liver indicating a fatty liver disease. The circular pattern in the biopsy image, as highlighted by arrows, indicates that the liver has a fatty liver disease. However, the circular pattern is not visible or detectable by investigating an ultrasound image (FIGS. 4A and 4C). The circular pattern is visible in the enhanced ultrasound images generated through the present solution, as shown in FIG. 4D generated from a B-mode ultrasound image FIG. 4C. As such, the present solution provides a method for a medical practitioner to make a liver or kidney disease diagnosis based solely on ultrasound data and circumvent the need to obtain a biopsy specimen.

Figure 2:
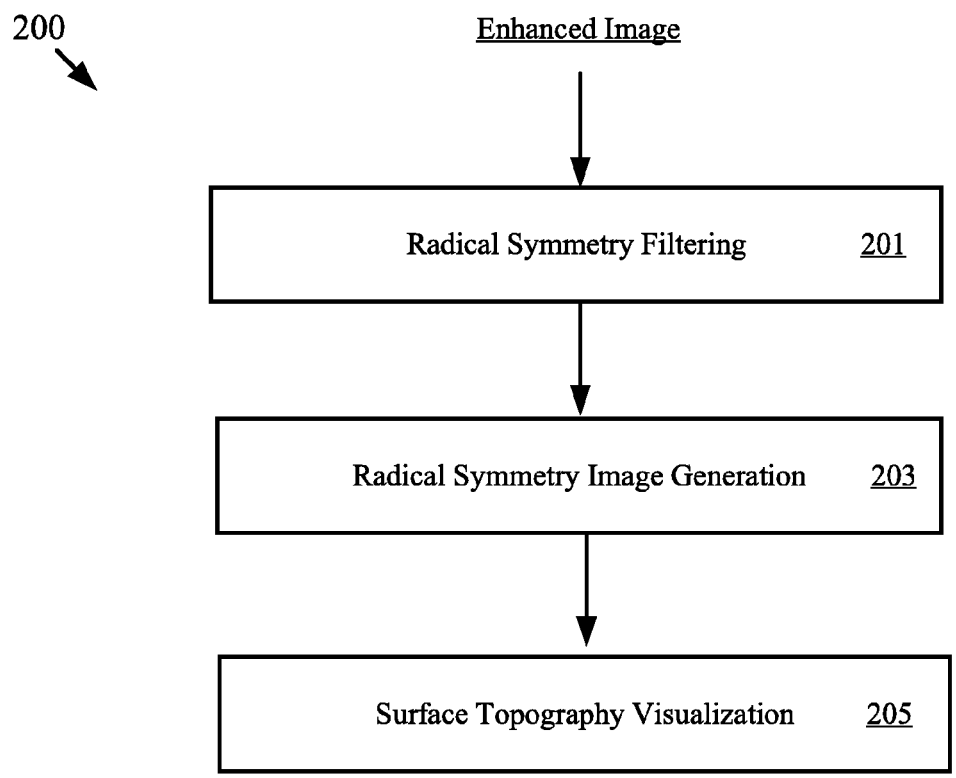
FIG. 2 shows an example of a process for generating a radial symmetry image.

Referring now to FIG. 2, a method for generating radial symmetry image based on the enhanced ultrasound images is provided. The process begins at 201 with by performing radial symmetry filtering the enhanced ultrasound images. The enhanced ultrasound images are further processed by utilizing local radial symmetry to identify the regions of interest in the enhanced images. The analysis relies on the fact that the diseased liver has a higher degree of radial symmetry compared to the healthy liver. The analysis is carried out by searching for dark spherical shapes in the enhanced images using the fast radial feature detection algorithm. At 203, the process includes generating radial symmetry images, as shown in FIGS. 5-6. FIG. 5B shows surface topography visualization of radial symmetry image corresponding to normal/healthy liver tissue; FIG. 5C shows surface topography visualization of radial symmetry image corresponding to normal/healthy liver tissue, with different radial symmetry filter parameters applied as compared to FIG. 5B. FIG. 6B shows surface topography visualization of radial symmetry image corresponding to diseased liver tissue; FIG. 6C shows surface topography visualization of radial symmetry image corresponding to diseased liver tissue, with different radial symmetry filter parameters applied as compared to FIG. 6B. At 205, the process optionally includes outputting a surface topography map based on the radial symmetry image. The fast radial symmetry algorithm is described in detail below.

Fast radial symmetry was used for processing multimedia images. For each radius n, the algorithm uses image gradients to vote for both the positively and negatively affected pixels. These pixels are calculated using Equations (8) and (9):

$$p_{+ve}(p) = p + \text{round}\left(\frac{g(p)}{\|g(p)\|}n\right) \quad (8)$$

$$p_{-ve}(p) = p - \text{round}\left(\frac{g(p)}{\|g(p)\|}n\right) \quad (9)$$

In the above equations "round" rounds each vector element to the nearest integer, "g" is the gradient of the image (e.g., the gradient of the enhanced images), "n" represents the radius value for the spherical structures searched in the image. $p_{-ve}$ and $p_{+ve}$ correspond to pixels with gradient g(p) pointing towards and away from the center respectively. Using these pixels and orientation and magnitude projection images, denoted as $O_n$ and $M_n$ respectively, are calculated. For each of the affected pixel, the corresponding point $p_{+ve}$ in $O_n$ and $M_n$ is increased by 1 and $\|g(p)\|$ respectively. Similarly, for the negatively affected pixel, the corresponding point is decreased by the same quantity in each image, as defined by Equations (10)-(13):

$$O_n(p_{+ve}(p))=O_n(p_{+ve}(p))+1 \tag{10}$$

$$O_n(p_{-ve}(p))=O_n(p_{-ve}(p))-1 \tag{11}$$

$$M_n(p_{+ve}(p))=M_n(p_{+ve}(p))+\|g(p)\|, \tag{12}$$

$$M_n(p_{-ve}(p))=M_n(p_{-ve}(p))-\|g(p)\|, \tag{13}$$

Using these images, a radial symmetry response image is defined as: $S_n=F_n*A_n$ where "*" denotes the convolution operation. $A_n$ is an isotropic Gaussian function and $F_n$ is defined in Equations (14) and (15):

$$F_n(p) = \frac{M_n(p)}{k_n}\left(\frac{|\widetilde{O}_n(p)|}{k_n}\right)^\alpha \tag{14}$$

$$\widetilde{O}_n(p) = \begin{cases} O_n(p), & O_n(p) < k_n \\ k_n, & \text{otherwise} \end{cases} \tag{15}$$

Here $\alpha$ is a radial strictness parameter, and $k_n$ is a scaling factor across different radii. The final full radial symmetry transform is defined by performing this operation for various radii values and summing the resulting feature maps as in Equation (16):

$$S = \frac{1}{|N|}\sum_{n \in N} S_n \tag{16}$$

The final topography images are obtained by displaying a topography map based on the image intensity values above the radial symmetry and phase images. The diseased liver has a higher topography compared to healthy liver. Examples of surface topography images are shown in FIGS. 5D-E for a healthy liver and FIGS. 6D-E for a diseased liver. Specifically, FIG. 5D shows surface topography visualization of an enhanced ultrasound image corresponding to normal/healthy tissue; FIG. 5E shows surface topography visualization of an enhanced ultrasound image corresponding to normal/healthy tissue, with different filter parameters used as compared to FIG. 5D. FIG. 6D shows surface topography visualization of an enhanced ultrasound image corresponding to diseased tissue; FIG. 6E shows surface topography visualization of an enhanced ultrasound image corresponding to diseased tissue, with different filter parameters used as compared to FIG. 6D.

Figure 7:
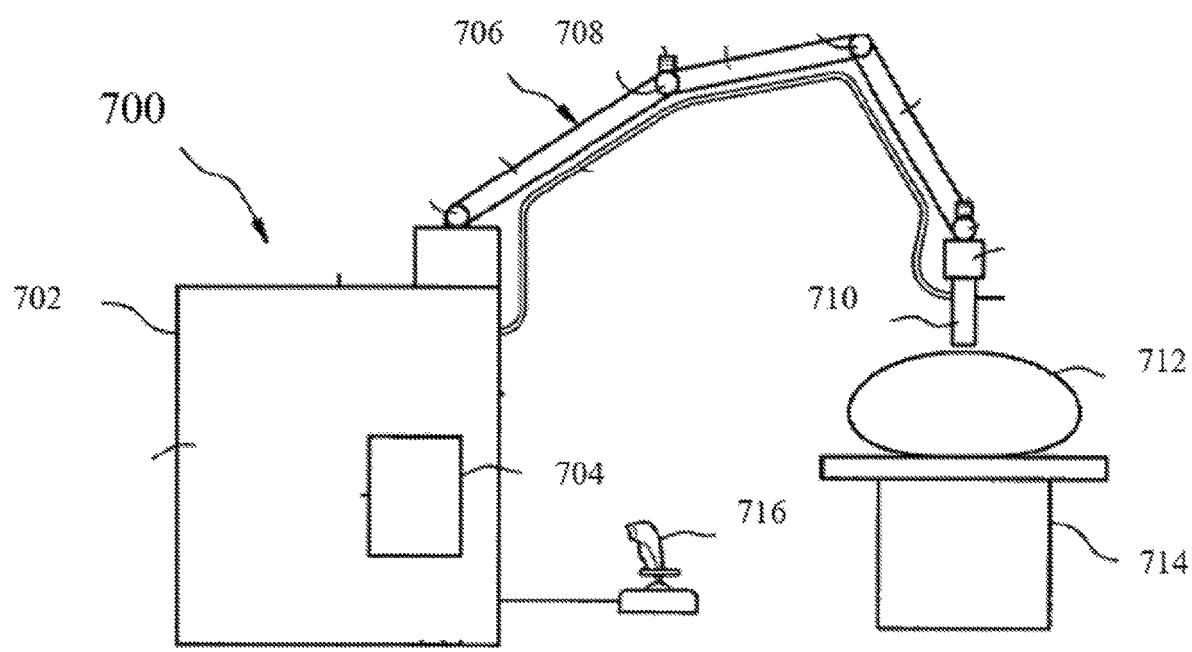
FIG. 7 is a schematic illustration of an exemplary ultrasound device in which the present solution can be implemented.

Referring now to FIG. 7, there is provided a schematic illustration of an exemplary ultrasound device 700 in which the present solution can be implemented. The ultrasound device 700 comprises a device stand 702 in which a computing device 704 is disposed. Computing device 704 is generally configured to control the operations of the ultrasound device 700. Such control can be in response to user-software interactions via an input device 716 and/or in accordance with pre-defined rules. A robotic arm 706 is movably attached to the device stand 702. The robotic arm 706 includes, but is not limited to, an articulating arm with a plurality of joints 708. An ultrasound transducer 710 is disposed at a distal end of the robotic arm 706. The ultrasound transducer 710 is moved over an object's surface 712 to be examined and generates a raw ultrasound signal. The object is arranged on a patient positioning table 714. The raw ultrasound signal is provided to the local computing device 704 or a remote computing device for processing in accordance with the present solution. The results of this processing is a transformation of the raw ultrasound data into an enhanced ultrasound image (e.g., such as that shown in FIG. 4).

Figure 8:
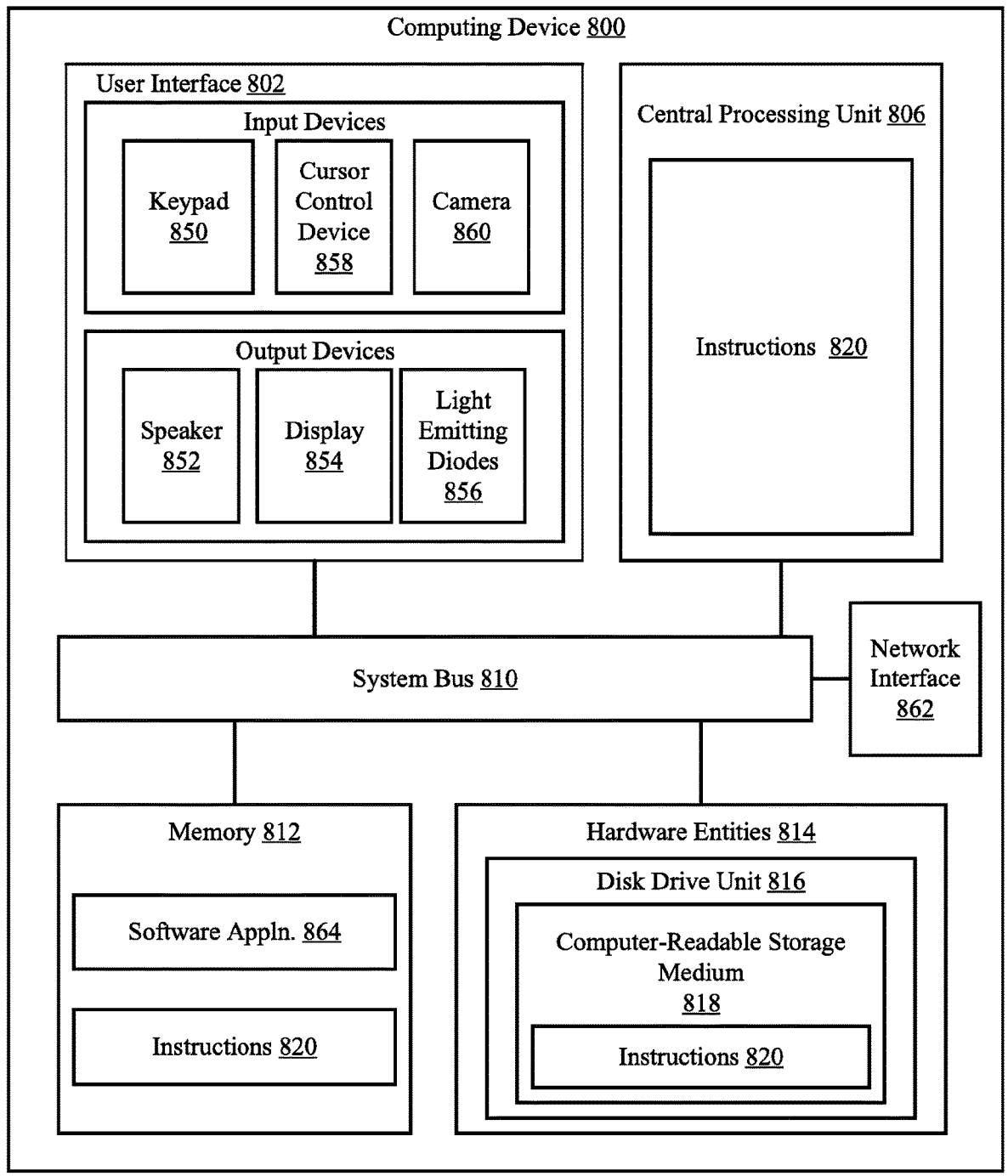
FIG. 8 is a schematic illustration of an exemplary architecture for a computing device.

Referring now to FIG. 8, there is provided an illustration of an exemplary architecture for a computing device 800. Computing device 800 may be local to an ultrasound device (e.g., the ultrasound device 700 of FIG. 7). In this case, computing device 704 is the same as or substantially similar to computing device 800. In other scenarios, the computing device 800 is located remote from the ultrasound device. In this case, the computing device 704 of the ultrasound device includes a network interface that facilitates communication between the two computing devices over a network (e.g., the Intranet or Internet).

Computing device 800 may include more or fewer components than those shown in FIG. 8. However, the components shown are sufficient to disclose an illustrative embodiment implementing the present solution. The hardware architecture of FIG. 8 represents one embodiment of a representative computing device configured to facilitate the generation of an enhanced ultrasound image based on a raw ultrasound signal. As such, the computing device 800 of FIG. 8 implements at least a portion of a method for providing such an enhanced ultrasound image in accordance with the present solution.

Some or all the components of the computing device 800 can be implemented as hardware, software and/or a combination of hardware and software. The hardware includes, but is not limited to, one or more electronic circuits. The electronic circuits can include, but are not limited to, passive components (e.g., resistors and capacitors) and/or active components (e.g., amplifiers and/or microprocessors). The passive and/or active components can be adapted to, arranged to and/or programmed to perform one or more of the methodologies, procedures, or functions described herein.

As shown in FIG. 8, the computing device 800 comprises a user interface 802, a Central Processing Unit ("CPU") 806, a system bus 810, a memory 812 connected to and accessible by other portions of computing device 800 through the system bus 810, and hardware entities 814 connected to system bus 810. The user interface can include input devices (e.g., a keypad 850, a cursor control device 858, and/or a camera 860) and output devices (e.g., speaker 852, a display 854, and/or light emitting diodes 856), which facilitate user-software interactions for controlling operations of the computing device 800.

At least some of the hardware entities 814 perform actions involving access to and use of memory 812, which can be a Random Access Memory ("RAM"), a disk driver and/or a Compact Disc Read Only Memory ("CD-ROM"). Hardware entities 814 can include a disk drive unit 816 comprising a computer-readable storage medium 818 on which is stored one or more sets of instructions 820 (e.g., software code) configured to implement one or more of the methodologies, procedures, or functions described herein. The instructions 820 can also reside, completely or at least partially, within the memory 812 and/or within the CPU 806 during execution thereof by the computing device 800. The memory 812 and the CPU 806 also can constitute machine-readable media. The term "machine-readable media," as used here, refers to a single medium or multiple media (e.g., a centralized or distributed database, and/or associated caches and RPUs) that store the one or more sets of instructions 820. The term "machine-readable media," as used here, also refers to any medium that is capable of storing, encoding or carrying a set of instructions 820 for execution by the computing device 800 and that cause the computing device 800 to perform any one or more of the methodologies of the present disclosure.

In some scenarios, the hardware entities 814 include an electronic circuit (e.g., a processor) programmed for facilitating the provision of an enhanced ultrasound image. In this regard, it should be understood that the electronic circuit can access and run a software application 864 installed on the computing device 800. The software application 824 is generally operative to facilitate the generation of the enhanced ultrasound image. Other functions of the software application 864 will become apparent as the discussion progresses.

The software application 864 implementing the present solution described herein is stored as a software program in a computer-readable storage medium and is configured for running on the CPU 806. Furthermore, software implementations of the present solution can include, but are not limited to, distributed processing, component/object distributed processing, parallel processing, virtual machine processing. In the various scenarios, a network interface device 862 connected to a network environment communicates over the network using the instructions 820.

The present solution may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

As used in this document, the singular form "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

All of the apparatus, methods, and algorithms disclosed and claimed herein can be made and executed without undue experimentation in light of the present disclosure. While the invention has been described in terms of preferred embodiments, it will be apparent to those having ordinary skill in the art that variations may be applied to the apparatus, methods, and sequence of steps of the method without departing from the concept, spirit, and scope of the invention. More specifically, it will be apparent that certain components may be added to, combined with, or substituted for the components described herein while the same or similar results would be achieved. All such similar substitutes and modifications apparent to those having ordinary skill in the art are deemed to be within the spirit, scope, and concept of the invention as defined.

The features and functions disclosed above, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

What is claimed is:

1. A system for generating a liver ultrasound image, comprising:
   a non-transitory, computer readable memory;
   one or more processors; and
   a computer-readable medium containing programming instructions that, when executed by the one or more processors, cause the system to:
   acquire a raw liver ultrasound signal output from an ultrasound device;
   generate filtered liver ultrasound image data by filtering the raw liver ultrasound signal to transform information from a signal domain to a frequency domain;
   extract image phase and energy features from the filtered liver ultrasound image data by an alpha scale filtering that is configured to extract the image phase features;
   generate a filtered liver ultrasound signal by transforming the image phase and energy features from the frequency domain to the signal domain;
   produce a transmission map estimation based on a backscattered liver ultrasound signal from a tissue interface; and
   enhance the image phase and energy features of the filtered liver ultrasound signal based on the transmission map estimation so that portions of a soft liver tissue associated therewith are made darker or lighter in an enhanced liver ultrasound image.

2. The system of claim 1, further comprising programming instructions, when executed by the one or more processors, causing the system to
   perform radial symmetry filtering on the enhanced liver ultrasound image by analyzing dark spherical shapes in the enhanced liver ultrasound image; and
   generate a radial symmetry image to identify regions of interest in the enhanced liver ultrasound image.

3. The system of claim 2, further comprising programming instructions, when executed by the one or more processors, causing the system to output a surface topography map based on the radial symmetry image.

4. The system of claim 1, wherein the alpha scale filtering is performed in a frequency domain.

5. The system of claim 4, wherein the alpha scale filtering is defined by expression $$ASF(\omega) = \begin{cases} n_c \omega^a \exp(-(\sigma\omega)^{2\alpha}) & \omega > 0 \\ 0 & \text{otherwise} \end{cases}$$

where a is constant derivative parameter, σ is a filter alpha-scale parameter, and $n_c$ is a unit normalization constant calculated from filter α.

6. The system of claim 5, wherein $n_c$ is computed in accordance with mathematical equation $$n_c = 2\frac{\sqrt{\pi\alpha}\, 2^{\frac{2a+1}{4\alpha}} s^{a+0.5}}{\sqrt{\Gamma\left(\frac{2a+1}{2\alpha}\right)}}$$

where s is a scale parameter and α is a derivative parameter.

7. The system of claim 1, wherein the transmission map estimation comprises combining scattering and attenuation effects in soft tissue based on equation $$US(x,y) = US_A(x,y)US_E(x,y) + (1 - US_A(x,y))\alpha$$

where US(x,y) is a local energy image, $US_A(x, y)$ is a signal transmission map, $US_E(x, y)$ is an enhanced ultrasound image, and α is a constant value representative of echogenicity in the soft tissue in a local region.

8. The system of claim 7, wherein $US_E(x, y)$ is extracted by estimating the signal transmission map $US_A(x, y)$ using a Beer-Lambert law which models an attenuation function as a function of imaging depth.

9. The system of claim 8, wherein the Beer-Lambert law is defined by equation $$US_T(x,y) = US_o(x,y)\exp(-\eta d(x,y))$$

where $US_o(x, y)$ is an initial intensity image, $US_T(x, y)$ is an attenuated intensity image, $\eta$ is an attenuation coefficient, and d(x,y) is a distance from an ultrasound transducer surface.

10. The system of claim 9, wherein $US_A(x,y)$ is obtained by minimizing an objective function defined by equation $$\frac{\lambda}{2}\|US_A(x,y) - US_T(x,y)\|_2^2 + \sum_{j\in\omega}\|W_j o (D_j * US_A(x,y))\|_1$$

where ω is an index set, o represents element wise multiplication, * is a convolution operation, $D_j$ is obtained using a bank of high order differential filters consisting of eight Kirsch filters and one Laplacian filter, and $W_j$ is a weighting matrix calculated in accordance with mathematical equation $$W_j = \exp(-|D_j(x,y) * US(x,y)|^2).$$

11. The system of claim 10, wherein $US_E(x, y)$ is calculated in accordance with equation $$US_E(x,y) = \left[\frac{US(x,y) - \alpha}{[\max(US_A(x,y), \varepsilon)]^\delta}\right] + \alpha.$$

12. The system of claim 2, wherein the radial symmetry filtering is specified by equation $$S_n = F_n * A_n$$

where "*" denotes the convolution operation; $A_n$ is an isotropic Gaussian function and $F_n$ is defined as:

$$F_n(p) = \frac{M_n(p)}{k_n}\left(\frac{|\widetilde{\mathcal{O}_n}(p)|}{k_n}\right)\alpha$$

$$\widetilde{\mathcal{O}_n}(p) = \begin{cases} O_n(p), & O_n(p) < k_n \\ k_n, & \text{otherwise} \end{cases}$$

and a is a radial strictness parameter, and $k_n$ is a scaling factor across different radii.

13. The system of claim 2, wherein the radial symmetry image is defined by equation $$S = \frac{1}{|N|}\sum_{n\in N} S_n$$

where S is a sum of all symmetry contributions $S_n$ over all ranges considered, and n is the number of symmetry contributions over all radiuses considered.

14. A method for generating a liver ultrasound image, comprising:
acquiring, by a computing device, a raw liver ultrasound signal output from an ultrasound device;
generating filtered liver ultrasound image data by filtering the raw liver ultrasound signal to transform information from a signal domain to a frequency domain;
extracting image phase and energy features from the filtered liver ultrasound image data by an alpha scale filtering that is configured to extract the image phase features;
generating a filtered liver ultrasound signal by transforming the image phase and energy features from the frequency domain to the signal domain;
producing a transmission map estimation based on a backscattered liver ultrasound signal from a tissue interface; and
enhancing the image phase and energy features of the filtered liver ultrasound signal based on the transmission map estimation so that portions of a soft liver tissue associated therewith are made darker or lighter in an enhanced liver ultrasound image.

15. The method of claim 14, further comprising:
performing, by a computing device, radial symmetry filtering on the enhanced liver ultrasound image by analyzing dark spherical shapes in the enhanced liver ultrasound image; and
generating, by a computing device, a radial symmetry image to identify regions of interest in the enhanced liver ultrasound image.

16. The method of claim 15, further comprising outputting a surface topography map based on the radial symmetry image.

17. The method of claim 14, wherein the backscattered liver ultrasound signal is modulated by interactions with a liver tissue, the interactions comprising scattering and attenuation.

18. The method of claim 14, wherein the step of generating the filtered liver ultrasound image data is performed by a Fourier transform.

19. The method of claim 14, wherein the step of generating the filtered liver ultrasound signal is performed by the inverse Fourier transform.

20. The method of claim 14, wherein the alpha scale filtering is defined by expression $$ASF(\omega) = \begin{cases} n_c \omega^\alpha \exp(-(\sigma\omega)^{2\alpha}) & \omega > 0 \\ 0 & \text{otherwise} \end{cases}$$

where $\alpha$ is constant derivative parameter, $\sigma$ is a filter alpha-scale parameter, and $n_c$ is a unit normalization constant calculated from filter $\alpha$.

* * * * *